United States Patent [19]

Dalto et al.

[11] Patent Number: 5,074,843
[45] Date of Patent: Dec. 24, 1991

[54] DEVICE FOR SUBCUTANEOUS INJECTION WITHOUT A NEEDLE

[76] Inventors: Tino Dalto, 30, Rue Trachel, 06000 Nice; Claude Laruelle, 18, Avenue Bellevue, 06270 Villeneuve Loubet, both of France

[21] Appl. No.: 499,505

[22] PCT Filed: Nov. 3, 1989

[86] PCT No.: PCT/FR89/00572
§ 371 Date: Jul. 2, 1990
§ 102(e) Date: Jul. 2, 1990

[87] PCT Pub. No.: WO90/04989
PCT Pub. Date: May 17, 1990

[30] Foreign Application Priority Data
Nov. 3, 1988 [FR] France ............... 88 15376

[51] Int. Cl.⁵ .................................. A61M 5/30
[52] U.S. Cl. ..................... 604/68; 604/134; 604/135
[58] Field of Search ............. 604/48, 68–72, 604/134–136, 140–143, 264

[56] References Cited

U.S. PATENT DOCUMENTS

| | | |
|---|---|---|
| 2,681,653 | 6/1954 | Kuhne . |
| 3,140,713 | 7/1964 | Ismach . |
| 3,788,315 | 1/1974 | Laurens . |
| 3,802,430 | 4/1974 | Schwebel et al. . |

FOREIGN PATENT DOCUMENTS

| | | |
|---|---|---|
| 276158 | 7/1988 | European Pat. Off. . |
| 2620338 | 3/1989 | France . |
| 1333215 | 10/1073 | United Kingdom . |
| 677523 | 8/1952 | United Kingdom . |

OTHER PUBLICATIONS

P. N. Bissell et al., "EXIT the Needle", *Engineering*, vol. 211, No. 8, Nov. 1971, pp. 901–905.

*Primary Examiner*—Max Hindenburg
*Assistant Examiner*—Steven J. Shumaker
*Attorney, Agent, or Firm*—Bell, Seltzer, Park & Gibson

[57] ABSTRACT

A device for subcutaneous injection without a needle comprising an injection head (12) including a plurality of injection holes (38) having a diameter of less than about 100 microns, these holes being parallel to one another and being formed at the ends of larger-diameter oblique cylindrical ducts (42) made through the thickness of the injection head.

8 Claims, 2 Drawing Sheets

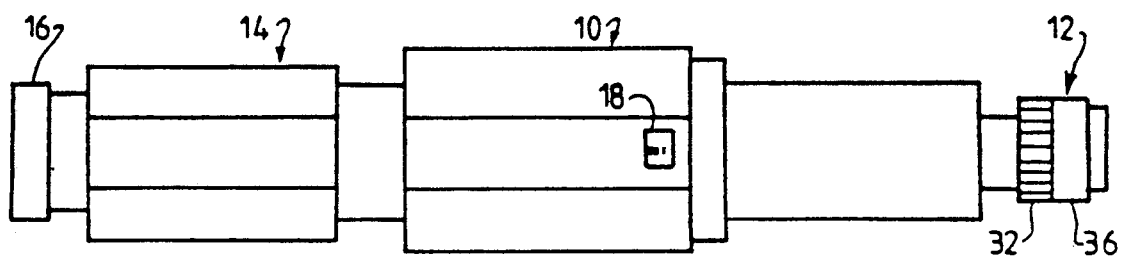
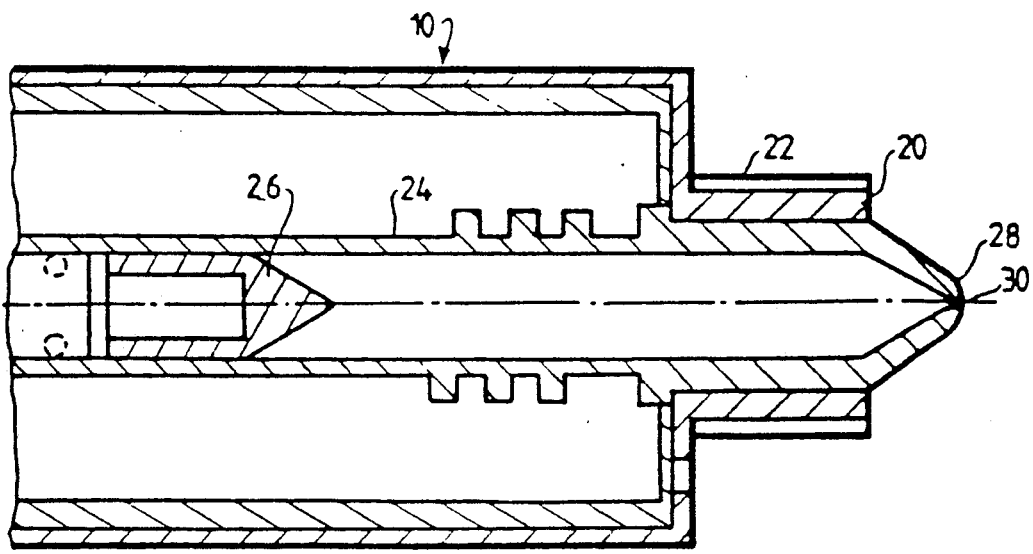

DEVICE FOR SUBCUTANEOUS INJECTION WITHOUT A NEEDLE

The invention relates to a device for subcutaneous injection without a needle.

Devices if this type have been known for a long time comprising a tubular body in which a piston is guided in reciprocating motion. An open end of the tubular body receives the injection head which includes a hole of very small diameter, generally in the range 0.2 mm to 1 mm. The piston received in the tubular body is associated with a spring thrust mechanism including means for locking it in a compressed position and for unlocking or releasing it.

The mechanical substance to be injected is sucked in through the open end of the tubular body and is contained in said end. The injection head is then mounted on said end of the tubular body, after which unlocking the thrust mechanism causes the piston to expel the substance through the very small hole in the injection head which is applied to the skin of the patient. The medicinal substance is then sprayed very finely and passes through the skin of the patient.

This method of injecting a medicinal substance is less traumatizing than using a conventional syringe with a needle. However, it is often observed that the skin of the patient is damaged at the point of injection, and that hematomas rapidly form due to blood vessels being ruptured. The patient may also feed quite sharp pain at the moment the substance is injected.

The object of the invention is to avoid these drawbacks.

The object of the present invention is to provide a device for subcutaneous injection without a needle, enabling the pain felt at the moment of injection to be considerably reduced, avoiding damage to the skin of the patient, and not creating hematomas, while nevertheless ensuring that a predetermined dose of medicinal substance is injected.

To this end, the present invention provides a device of the above-specified type for subcutaneous injection without a needle, the device comprising a tubular body having an injection head mounted at one end thereof, a piston guided to move inside the body, and a piston thrust mechanism housed inside the body and associated with locking means and with release means, the device being characterized in that the injection head comprises a plurality of injection holes having a diameter of less than about 100 microns.

The presence of a plurality of very fine injection holes having a diameter of less than about 100 microns in the above-specified head makes it possible to reduce by a factor equal to the number of holes: the time during which the substance is injected; the risk of hematomas forming; and the pain felt by the patient. The very small diameter of the injection holes makes it possible to spray the medicinal substance very finely and facilitates its passage through the skin of the patient.

According to another characteristic of the invention, the injection holes are parallel to one another and they are oriented perpendicularly to that surface of the injection head through which they open out.

The substance which is injected via these holes runs a smaller risk of rising beneath the skin of the patient than it would if it had been injected via obliquely oriented holes.

According to yet another characteristic of the invention, each injection hole is situated at the end of a cylindrical duct formed through the thickness of the injection head and having a diameter which is larger than the diameter of the injection hole, e.g. a diameter in the range 0.5 mm to 1 mm.

The presence of this cylindrical duct facilitates forming an injection hole of very small diameter.

According to yet another characteristic of the invention the injection head is made of stainless steel and the injection holes are not less than 0.5 mm long.

This characteristic is important insofar as shorter injection holes run the risk of metal flaking from around the holes because of the very high injection pressure through the holes.

in a preferred embodiment of the invention, the injection head is crimped onto a ring having an internal thread, thereby enabling the head to be screwed onto the end of the tubular body.

The injection head is thus made interchangeable and it can be sterilized easily. In addition, it is possible to select a particular type of injection head as a function of the substance to be injected, and of the location of the injection zone on the body of the patient.

For example, the injection holes may be distributed around a circle having a diameter of about 8 to 10 mm, in particular for injecting insulin, or around a circle having a diameter in the range about 2 mm to about 4 mm, in particular for injecting anesthetic in dental surgery, or around a circle having a diameter lying in the range about 15 mm to about 20 mm, in particular for mesotherapy.

The invention will be better understood and other characteristic details and advantages thereof will appear more clearly from reading the following description given by way of example and made with reference to the accompanying drawings, in which:

FIG. 1 is a diagram of a device of the invention;

FIG. 2 is a fragmentary view in longitudinal section and on a larger scale showing the end of the tubular body of the FIG. 1 device.

Figure 3:
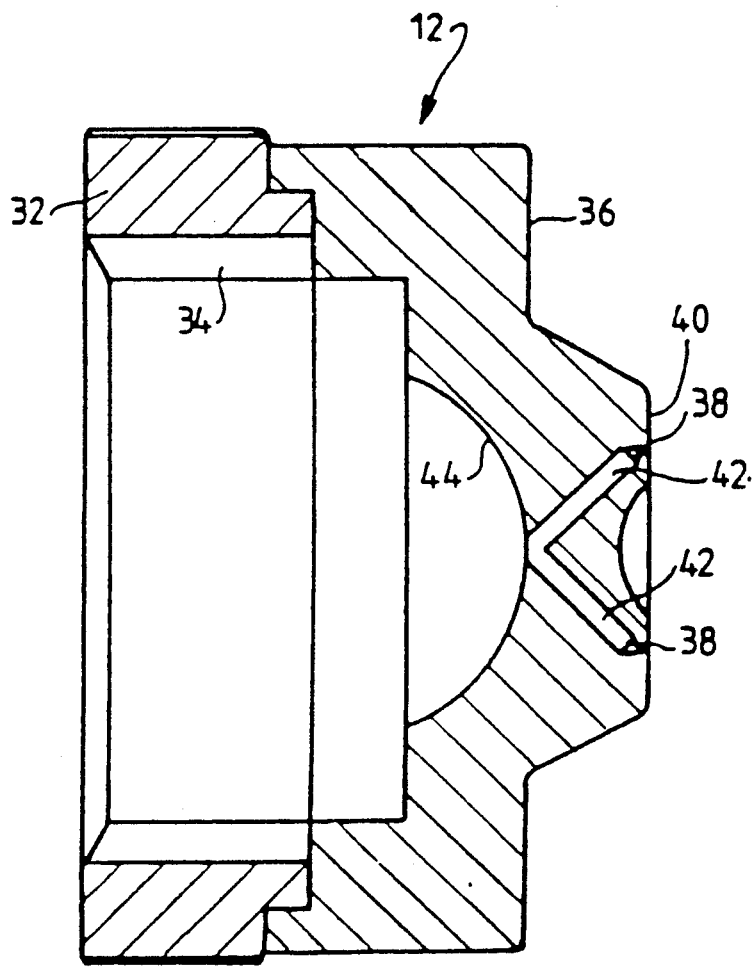
FIG. 3 is a longitudinal section on an even larger scale through an injection head for screwing onto the end of the tubular body shown in FIG. 2. Reference is made initially to FIG. 1 which is a diagrammatic overall view of an injection device of the invention.

This device comprises a tubular body designated by reference 10 having an injection head 12 of the invention mounted at one end thereof. A conventional type of spring thrust mechanism is housed in a cylinder 14 and is associated with spring compression locking means and with unlocking or release means, e.g. of the type including a pushbutton 16. This thrust mechanism acts on a piston guided to move inside the tubular body 10 and intended to propel a medicinal substance through the extremely fine holes in the injection head 12.

In conventional manner, the thrust mechanism 14 is mountable as a whole by screwing inside the body 10 with its longitudinal position inside said body determining the dose of substance to be injected. For example, the tubular body 10 may include a small window 18 through which graduations carried by a portion of the mechanism 14 can be seen, which graduations correspond to quantities of substance to be injected.

Reference is now made to FIG. 2 which shows the end of the body 10 on which the injection head 12 is mounted by screwing.

For this purpose, the end of the body 10 includes a tubular cylindrical extension 20 having an outside thread 22 which receives in sealed manner the end of a cylindrical tube 24 inside which the piston 26 for propelling the substance to be injected is guided. The free end of the tube 24 is substantially conical in shape having a rounded apex 28 including an axial hole 30 of small diameter e.g. about 1 mm.

The injection head 12 shown on a larger scale still in longitudinal section in FIG. 3 includes an annular ring 32 having an inside thread 34 enabling it to be screwed onto the cylindrical end 20 of the body 10, and an injection head per se 36 which is in the form of a cap and which is fixed to the annular ring 32, e.g. by crimping.

The part 36 is made of stainless steel and includes a plurality of injection holes 38 of very small diameter, less than 100 microns, and lying, for example, in the range 10 microns to 100 microns.

These holes 32 are parallel to each other and they extend perpendicularly to the plane outside face 40 of the injection head (with the face 40 constituting the face of the injection head which is applied against the skin of a patient).

For reasons of convenience in manufacture, the injection holes 38 are rectilinear and they are formed at the ends of larger diameter cylindrical ducts 42 (duct diameter in the range 0.5 mm to 1 mm, for example), which ducts extend obliquely and are joined together at their inside ends substantially on the longitudinal axis of the head 12.

The common inside ends of the cylindrical ducts 42 open out in a rounded concave surface 44 of the part 36, said surface 44 having a radius of curvature which corresponds substantially to that of the rounded end 28 of the tube 24 shown in FIG. 2. As a result, when the ring 12 is screwed onto the threaded end 20 of the body 10, the rounded tip 28 of the tube 24 bears against the rounded concave surface 44 of the head 12 with the axial hole 30 of the tube 24 being directly in line with the common ends of the cylindrical ducts 42.

It is also important for the injection holes 38 to be at least 0.5 mm long in order to avoid the metal of the part 36 flaking away while substance is being injected.

The injection holes 38 are drilled into the injection head using very fine drill bits. Other techniques could be used, e.g. electroerosion or a laser beam.

The number of injection holes 38 may lie in the range 2 to about 10, said holes being distributed around a circle whose radius may vary fairly widely as a function of the type of substance to be injected and also as a function of the location of the point of injection on the bodies of patients.

For example, when injecting insulin, there may be two or three holes 38 distributed around a circle having a diameter in the range about 8 mm to about 10 mm.

For injecting an anaesthetic in dental surgery, the holes should be distributed around a smaller circle, having a diameter in the range about 2 mm to about 4 mm.

In mesotherapy, the number of holes should be larger and the holes should be distributed around a circle having a diameter in the range about 15 mm to about 20 mm.

It is has been observed that the injection head of the invention makes it possible to inject medicinal substances practically painlessly, without causing lesions in the skin and without hematomas appearing. When the injection pressure is properly adjusted, by tightening or loosening the thrust mechanism 14, the skin remains dry after injection which means that all of the substance has been injected beneath the skin and there is no tendency for it to seep back out. In addition, there is usually no droplet of blood at the point of injection.

We claim:

1. A device for subcutaneous injection without a needle comprising a tubular body having an injection head mounted at one end thereof, a plurality of injection holes formed in said injection head, said holes having a diameter of less than about 100 microns, a piston mounted for slidable movement within said tubular body, cylindrical ducts extending through said injection head and communicating with said injection holes, said cylindrical ducts each having a diameter larger than the diameter of said injection holes and being in the range of about 0.5 mm to 1.0 mm, and wherein said tubular body includes an outer convex surface positioned at the end on which said injection head is mounted, and said injection head includes an integrally formed concave surface complementary in shape to said convex surface on said tubular body, and wherein said cylindrical ducts are directed toward said piston and open out into said concave surface formed in said injection head, and a piston thrust mechanism carried by said tubular body and engaging said piston for acting on said piston and moving said piston within said body to propel a medicinal substance through said injection holes.

2. A device according to claim 1 wherein said injection head includes a substantially planar outer face and said injection holes are parallel to each other and extend substantially perpendicular through said substantially planar outer face of said injection head.

3. A device according to claim 1 wherein said injection holes are about 10 to 100 microns in diameter.

4. A device according to claim 1 wherein said injection holes are positioned in a circular pattern having a diameter of about 8 mm to 10 mm.

5. A device according to claim 1 wherein said injection holes are distributed in a circular pattern having a diameter of about 2 mm to 4 mm.

6. A device according to claim 1 wherein said injection holes are distributed in a circular pattern having a diameter of about 15 mm to 20 mm.

7. A device according to claim 1 wherein said injection head is made of stainless steel and said injection holes are greater than 0.5 mm in length.

8. A device according to claim 1 wherein said tubular body includes a threaded end, and including a ring having an inside threaded portion dimensioned for threaded receipt on said threaded end of said tubular body, and wherein said injection head is crimped on said ring.

* * * * *